(12) United States Patent
Steinbacher

(10) Patent No.: US 9,797,832 B2
(45) Date of Patent: Oct. 24, 2017

(54) METHOD AND GAS ANALYZER FOR MEASURING THE CONCENTRATION OF A GAS COMPONENT IN A SAMPLE GAS

(71) Applicant: Siemens Aktiengesellschaft, Munich (DE)

(72) Inventor: Franz Steinbacher, Karlsruhe (DE)

(73) Assignee: Siemens Aktiengesellschaft, Munich (DE)

(*) Notice: Subject to any disclaimer, the term of this patent is extended or adjusted under 35 U.S.C. 154(b) by 19 days.

(21) Appl. No.: 15/027,883

(22) PCT Filed: Sep. 23, 2015

(86) PCT No.: PCT/EP2015/071841
§ 371 (c)(1),
(2) Date: Apr. 7, 2016

(87) PCT Pub. No.: WO2016/050577
PCT Pub. Date: Apr. 7, 2016

(65) Prior Publication Data
US 2016/0299065 A1    Oct. 13, 2016

(30) Foreign Application Priority Data

Sep. 29, 2014  (EP) .................................. 14186890

(51) Int. Cl.
*G01N 21/00* (2006.01)
*G01N 21/39* (2006.01)
(Continued)

(52) U.S. Cl.
CPC ................ *G01N 21/39* (2013.01); *G01J 3/42* (2013.01); *G01J 3/433* (2013.01); *H01S 5/0622* (2013.01);
(Continued)

(58) Field of Classification Search
CPC ............. G01N 21/39; G01N 2021/399; G01N 2021/0612; G01N 21/31; G01J 3/42;
(Continued)

(56) References Cited

U.S. PATENT DOCUMENTS 6,351,309 B1 *  2/2002  Bomse .................... G01N 21/39
                                                 250/343
7,116,422 B2 * 10/2006  Larking .................. G01J 3/433
                                                 356/437

(Continued)

OTHER PUBLICATIONS

Eichholz, R. et al., "Frequency modulation spectroscopy with a THz quantum-cascade laser", Optics Express 21(26), 32199 (2013).
(Continued)

*Primary Examiner* — Michael A Lyons
*Assistant Examiner* — Maurice Smith
(74) *Attorney, Agent, or Firm* — Cozen O'Connor

(57) ABSTRACT

Method and gas analyzer for measuring the concentration of a gas component in a sample gas, wherein to measure the concentration of a gas component in a sample gas, a laser diode is actuated by a current and light generated by the laser diode is guided through the sample gas to a detector, the current is simultaneously varied within periodically successive sampling intervals for the wavelength-dependent sampling of an absorption line of interest of the gas component, and the current can be additionally modulated sinusoidally based on wavelength modulation spectroscopy with a low frequency and small amplitude, such that a measuring signal generated by the detector is evaluated to form a measurement result, where to improve the measuring signal-noise ratio and achieve a much lower detection limit with the same measuring distance, the current is modulated with a high (RF) frequency in the GHz range so that no wavelength modulation occurs, and an RF modulation amplitude is selected at the maximum level using the linear control range (Continued)

of the laser diode where, before evaluation, the measuring signal is demodulated at the radio frequency.

14 Claims, 3 Drawing Sheets

(51) Int. Cl.
  *G01J 3/433* (2006.01)
  *H01S 5/062* (2006.01)
  *G01J 3/42* (2006.01)
  *G01N 33/00* (2006.01)

(52) U.S. Cl.
  CPC ...... *H01S 5/06213* (2013.01); *H01S 5/06216* (2013.01); *G01N 33/0009* (2013.01); *G01N 2021/399* (2013.01); *G01N 2201/0612* (2013.01); *G01N 2201/0691* (2013.01)

(58) Field of Classification Search
  CPC .... G01J 3/433; H01S 5/06213; H01S 5/0622; G01B 9/02004
  See application file for complete search history.

(56) References Cited

U.S. PATENT DOCUMENTS

| | | | |
|---|---|---|---|
| 7,251,034 B2* | 7/2007 | Kluczynski | G01J 3/4338 356/437 |
| 7,969,576 B1 | 6/2011 | Buckley et al. | |
| 2006/0098202 A1* | 5/2006 | Willing | G01N 21/3504 356/437 |
| 2006/0187976 A1* | 8/2006 | Mori | G01N 21/39 372/20 |
| 2014/0185035 A1* | 7/2014 | Depenheuer | G01J 3/42 356/73 |
| 2015/0085288 A1* | 3/2015 | Steinbacher | G01N 21/39 356/437 |
| 2015/0338342 A1* | 11/2015 | Muramatsu | G01N 21/39 356/409 |
| 2016/0047739 A1* | 2/2016 | Bitter | G01N 21/31 356/402 |

OTHER PUBLICATIONS

Sun, H. C. et al., "Combined wavelength and frequency modulation spectroscopy: a novel diagnostic tool for materials processing", Applied Optics 32(6), 885-893 (1993).

* cited by examiner

METHOD AND GAS ANALYZER FOR MEASURING THE CONCENTRATION OF A GAS COMPONENT IN A SAMPLE GAS

CROSS-REFERENCE TO RELATED APPLICATIONS

This is a U.S. national stage of application No. PCT/EP2015/071841 filed 23 Sep. 2015. Priority is claimed on European Application No. 14186890 filed 29 Sep. 2014, the content of which is incorporated herein by reference in its entirety.

BACKGROUND OF THE INVENTION

1. Field of the Invention

The invention relates to a method and a gas analyzer for measuring the concentration of a gas component in a sample gas.

2. Description of the Related Art

A method or gas analyzer in the form of a laser spectrometer are known from U.S. Pat. No. 7,969,576 B1, R. Eichholz et al: "Frequency modulation spectroscopy with a THz quantum-cascade laser", Optics Express 21(26), 32199 (2013), U.S. Pat. No. 6,351,309 B1, and H. C. Sun et al: "Combined wavelength and frequency modulation spectroscopy: a novel diagnostic tool for materials processing", Applied Optics 32(6), 885-893 (1993).

Laser spectrometers are in particular used for optical gas analysis in process metrology. In this case, a laser diode generates light in the infrared range, which is guided along a measuring distance in a process plant or a gas cell through a process gas (sample gas), and then detected. The wavelength of the light is tuned to a specific absorption line of the respective gas component to be measured, where the laser diode samples the absorption line periodically in a wavelength-dependent manner. To this end, the laser diode is actuated by a ramp-shaped or triangular current signal (injection current) within successive sampling intervals.

With direct absorption spectroscopy (DAS), the measuring signal generated by the detector is evaluated directly, where the concentration of the gas component to be measured is determined directly from the reduction in light intensity (absorption) detected at the site of the absorption line. It is disadvantageous that the detection occurs in an extremely low-frequency range in which the gas analyzer noise (e.g., laser noise, detector noise) and the noise from the measuring distance (caused by turbulence, particles) is very high.

To avoid this problem, the injection current for the laser diode is additionally modulated sinusoidally with a predefined frequency and amplitude. With wavelength modulation spectroscopy (WMS), this modulation is performed with a frequency much lower than the full width at half maximum (FWHM) of the absorption line, typically in the kHz range. The modulation amplitude is small compared to the ramp-shaped or triangular current signal, but on the other hand high enough to ensure that the resultant spectral modulation amplitude of the laser light is greater than the full width at half maximum (FWHM) of the absorption line. The absorption line profile is not linear. As a result, high-order harmonics are also generated in the measuring signal. The measuring signal is typically demodulated at an n-th overtone, preferably the second harmonic, using phase-sensitive lock-in technology and evaluated to form a measurement result for each sampling interval.

Due to the small modulation amplitude, the detection of the n-th harmonic is directly proportional to the n-th derivative of the direct measuring signal. In the ideal case of a Lorentz-shaped absorption line, the 2f measuring signal is, for example, maximum with a modulation index of 2.2 (the modulation index is the ratio of the spectral modulation amplitude to the full width at half maximum of the sampled absorption line). The further evaluation can, for example, be achieved by fitting (curve fitting) of the profile of the demodulated measuring signal (intended curve) to be expected in the ideal case and described analytically via an approximation model to the actual profile (actual curve) thereof. One of the parameters of the approximation model is proportional to the concentration of the gas component. Consequently, the result of the evaluation, and hence the measurement result obtained, is the concentration of the gas component to be measured.

With frequency modulation spectroscopy (FMS), the injection current for the laser diode is modulated with a very high radio frequency, which is comparable to or greater than the full width at half maximum of the absorption line and can, therefore, range from tens of 10 MHz up to the GHz range. RF modulation generates side bands spaced apart from the emission frequency by an integral multiple of the modulation frequency on both sides of the emission frequency of the laser diode. The modulation index is lower than it is with WMS and selected low enough to ensure that only the two first side bands of the modulated laser light have a significant amplitude. The absorption line is investigated with these side bands. As is also the case with WMS, in addition to the modulation of the wavelength, FMS also results in modulation of the intensity of the laser light, where wavelength modulation is dominant and the amplitude modulation only provides a small contribution to the measuring signal. Therefore, laser diodes to be used for FMS (for example, lead salt lasers or quantum cascade lasers) have to be suitable for wavelength modulation at the radio frequencies described and the detectors must also have a very large bandwidth. This means the components and structure of an FM spectrometer are very expensive and complex. In order to use detectors with a lower bandwidth, with two-tone FMS, the laser diode is modulated with two radio frequencies that are very close to one another and detection is performed at the beat frequency.

DAS, WMS and FMS have specific advantages and disadvantages. WMS and FMS are in particular advantageous for the measurement of low concentrations because they are more efficient at filtering noise out of the measuring signal. However, at higher concentrations, the approximations required for the evaluation of the measuring signal are increasingly inaccurate thus resulting in a greater measuring error. Moreover, FMS is very expensive and complex. The reverse applies with DAS; due to the greater sensitivity to noise, the measuring error is higher at low concentrations. However, since no approximate description of the absorption line is required, the measuring accuracy improves as the concentration increases because the effective signal is stronger. It is only at very high concentrations (absorption saturation) that the measuring method once again becomes more inaccurate.

The method or gas analyzer known from the aforementioned U.S. Pat. No. 7,969,576 B1 work based on WMS where, in addition to the n-th harmonic of the measuring signal, its first harmonic, i.e., the fundamental frequency of the modulation, is evaluated to normalize the measurement result.

The detection limit and limit of determination for the measurement of the concentration of the gas component is restricted by noise, which superimposes the measuring signal and is primarily composed of the noise of the gas analyzer (laser noise, detector noise) and the noise from the measuring distance (caused by turbulence, particles). The longer the measuring distance, the greater the absorption and the measuring signal obtained. The measurement of small concentrations requires a sufficiently long measuring distance.

SUMMARY OF THE INVENTION

It is an object of the invention to provide a method and gas analyzer in which the measuring signal-noise ratio is improved and a much lower detection limit with the same measuring distance is achieved.

These and other objects and advantages are achieved in accordance with the invention by providing a method in which the laser diode is modulated with a frequency selected as a function of the properties of the laser diode high enough to ensure that, unlike the case with WMS and FMS, no wavelength modulation of the light generated occurs. The wavelength of the light is set or changed via the internal temperature of the laser diode, where this internal temperature can in turn be set or changed via the power loss due to the laser current and via the ambient temperature. Therefore, wavelength modulation can only be performed at low modulation frequencies, maximum in the kHz range. On the other hand, at higher frequencies, only the intensity of the light, but not its wavelength, is modulated. For example, with the currently available VCSE lasers, wavelength modulation finishes at a few MHz (see, e.g., J. Chen et al: "Experimental characterization of the frequency modulation behavior of vertical cavity surface emitting lasers", Applied Physics Letters 91, 141105 (2007)).

The radio-frequency (RF) modulation in accordance with the invention copies the baseband of the measuring signal to be evaluated from the frequency range disrupted by the noise of the gas analyzer and the measuring distance close to DC into a radio frequency range in which this noise is longer present. Accordingly, the measuring signal demodulated at the frequency of the RF modulation contains the same analytical information (useful information) as the measuring signal resulting from the conventional actuation of the laser diode without the RF modulation in accordance with the invention and, to be precise, independently of whether only a ramp-shaped or triangular variation of the current of the laser diode is performed for purposes of the wavelength-dependent sampling of the absorption line of interest and for the evaluation of the measuring signal based on direct absorption spectroscopy (DAS) or additionally LF modulation of the current is performed for the purposes of an WMS evaluation of the measuring signal. The measuring signal demodulated at the frequency of the RF modulation can, therefore, be evaluated in the same way as the previously used measuring signal at the site thereof or in addition thereto.

With wavelength-dependent sampling of the absorption line of interest of the gas component by the periodic variation of the current of the laser diode, the signal component of the measuring signal resulting from the additional RF modulation of the laser diode changes proportionally to the same degree as the extremely low-frequency signal component (virtually identical component) of the measuring signal, which results from the actuation of the laser diode by the ramp-shaped or triangular current signal. Therefore, the two signal components can be evaluated individually or together, for example after addition, in accordance with DAS. The same also applies analogously to the evaluation of the measuring signal based on WMS. During RF modulation of the laser diode, no wavelength modulation of the light occurs, which would disrupt the WMS evaluation. As a result, the amplitude of the RF modulation can be selected as high as the linear actuation range of the laser diode allows. In each case, the amplitude of the RF modulation in accordance with the invention is many times higher than with low-frequency WMS modulation where the modulation index is to be selected as a function of the width of the absorption line to be sampled and FMS modulation, where the modulation index is even lower than with WMS.

The different measurements with respect to the evaluation of the measuring signal based on DAS and WMS can be performed simultaneously in each sampling interval or alternately in successive sampling intervals and their results linked to the measurement result, for example, by averaging.

RF modulation can be performed with only one frequency, but advantageously also with several or numerous frequencies, where the measuring signals demodulated at these frequencies are either evaluated individually based on WMS and/or DAS and then combined with the measurement result, such as by data fusion (or multi-sensor data fusion), in the simplest case added, or first combined and then evaluated. The combination of the measuring signals demodulated at several or numerous frequencies or the results of the individual evaluations thereof produces a correspondingly large amount of data suitable for evaluation. In this case, the distance between the frequencies used for the RF modulation must be large enough to ensure that the frequency bands to be evaluated do not overlap and in addition can be acquired cleanly by bandpass filtering. Unlike the useful information contained, the noise in the different frequency bands is not correlated. As a result, the signal-noise ratio is improved. The amplitudes of the superimposed RF modulations are selected such that the laser diode is actuated as far as possible within its linear control range.

The measurement based on WMS can be performed in the conventional way in that the current of the laser diode and, hence, the wavelength of the light generated is modulated with an additional frequency and the measuring signal in the baseband and the demodulated measuring signal from the higher frequency range are evaluated at a harmonic, in particular the second harmonic, of the additional frequency.

However, WMS can also be modified and expanded, as is disclosed, for example, in the subject matter of the older and still unpublished German patent application with the file reference DE102014215848.6. Here, low-frequency WMS modulation is performed with several additional frequencies, which are spaced apart from one another by twice the magnitude of the lowest additional frequency, i.e., for example, $f_{NF}$, $3f_{NF}$, $5f_{NF}$ and $7f_{NF}$. The WMS evaluation of the measuring signal or the RF demodulated measuring signal is performed at the second harmonics of these frequencies, i.e., $2f_{NF}$, $6f_{NF}$, $10f_{NF}$ and $14f_{NF}$, and at least one of the sum and difference frequencies thereof, i.e., $2f_{NF}$, $4f_{NF}$, $6f_{NF}$, $8f_{NF}$, $6f_{NF}$, $14f_{NF}$. Due to the non-linear shape of the absorption line, the measuring signal contains not only the multiples (harmonics) of the frequencies used during the modulation but also the sums and differences of these frequencies. The WMS modulation frequencies used are separated by twice the magnitude $2f_{NF}$ of the smallest modulation frequency $f_{NF}$. As a result, the sum and difference frequencies thereof either coincide with the second harmonics or lie exactly halfway therebetween. Therefore, the frequency components of the measuring signal are each separated by twice the magnitude $2f_{NF}$ of the smallest modulation frequency $f_{NF}$. The corresponding measuring signal components each have the same profiles so that they are superimposed in a constructive way and it is possible to obtain a correspondingly large amount of evaluable signal energy from the absorption. Unlike the signal components that are added together, the noise at the different frequencies is not correlated. As a result, a very high signal-noise ratio occurs during the evaluation to form the measurement result.

Additionally or supplementarily, the measuring signal or demodulated measuring signal can be evaluated at the modulation frequencies $f_{NF}$, $3f_{NF}$, $5f_{NF}$ and $7f_{NF}$.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For a further explanation of the invention, reference is made to the figures in the drawing, in which.

DETAILED DESCRIPTION OF THE EXEMPLARY EMBODIMENTS

Figure 1:
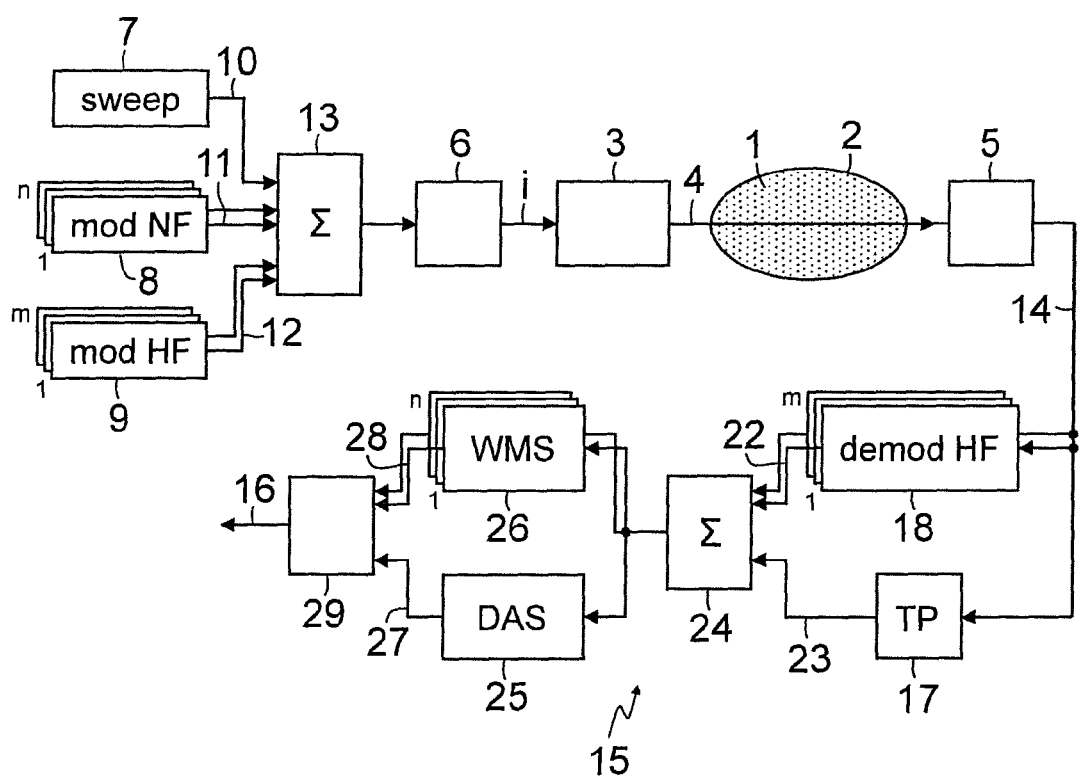
FIG. 1 a first exemplary embodiment of the gas analyzer in accordance with the invention.

FIG. 1 shows, in the form of a greatly simplified block diagram, a gas analyzer for measuring the concentration of at least one gas component of interest of a sample gas 1 contained in a measurement volume 2, such as a gas cell or a process gas line. The gas analyzer comprises a laser diode 3, the light 4 of which is incident on a detector 5 after passing through the sample gas 1. A controllable current source 6 feeds the laser diode 3 with an injection current i, where the intensity and the wavelength of the generated light 4 are functions of the current i and the operating temperature of the laser diode 3. For variation and modulation of the current i, a signal generator 7, a low-frequency (LF) modulation apparatus 8 and a radio-frequency (RF) modulation apparatus 9 generate different signals 10, 11, 12, which are fed to the current source 6 via a summing unit 13.

The signal 10 of the signal generator 7 varies the current periodically in accordance with a predefined, preferably ramp-shaped or triangular function to sample a selected absorption line of the gas component of interest with the more or less linear wavelength of the generated light 4. The signal 10 can additionally contain bursts, which succeed each other at regular distances, such as after each sampling period, and later enable normalization of the measurement.

The low-frequency (LF) modulation apparatus 8 is provided when the concentration of the gas component of interest is to be performed based on wavelength modulation spectroscopy (WMS). In this case, the current i, and hence the wavelength of the generated light 4, is modulated sinusoidally with a frequency in the kHz range and small amplitude. As indicated, the LF modulation can be expanded to n different frequencies.

The radio-frequency (RF) modulation apparatus 8 is used to modulate the current i with a radio frequency in the MHz range, for example, 50 MHz, and high amplitude. Here, the radio frequency is selected as a function of the properties of the laser diode 3 used such that only the intensity of the generated light 4 is modulated and no wavelength modulation occurs. The amplitude of the modulation is maximum within the linear control range of the laser diode 3. The amplitude can, for example, be within the range of magnitude of the half mean value of the current ramp (signal 10). Like LF modulation, RF modulation can also be expanded to several or numerous, here m, different frequencies. In this case, the distance between the frequencies must be large enough to ensure that the frequency bands to be evaluated based on WMS do not overlap and can be acquired cleanly by bandpass filtering after detection.

The detector 5 generates a measuring signal 14 as a function of the detected light intensity, where it is possible for the measuring signal to be automatically amplified and normalized with reference to the signal components resulting from the bursts of the signal 10. Furthermore, the measuring signal 14 is processed in an evaluation apparatus 15 to form a measurement result 16 identifying the concentration of the gas component of interest in the sample gas 1. Due to the RF modulation of the wavelength of the light 4, the baseband of the measuring signal 14 with the useful information contained therein is copied to higher frequency ranges. The useful information contained in the baseband is obtained by filtering the measuring signal 14 in a low-pass filter 17 with a cut-off frequency below the lowest of the RF modulation frequencies. In order to obtain the useful information from the higher frequency bands, the measuring signal 14 is demodulated parallel to the low-pass filtering in a RF demodulation apparatus 18 at each of the m (m≥1) RF modulation frequencies used.

Figure 2:
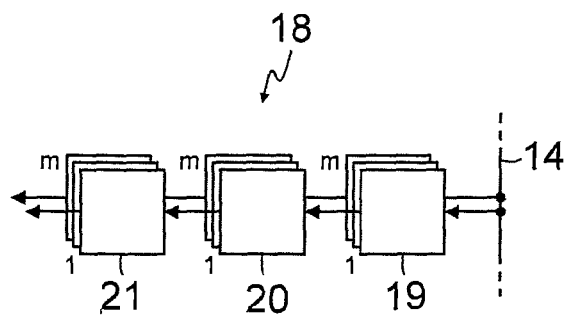
FIG. 2 an example of RF demodulation of a measuring signal.

As FIG. 2 shows, the demodulation is performed in m parallel channels, which each comprise a band-pass filter 19 and a lock-in amplifier 20 with a downstream low-pass filter 21. In this case, the band-pass filtered measuring signal 14 is demodulated in a phase-sensitive manner by multiplication with a reference signal at the respective RF demodulation frequency and the in-phase component, i.e., the useful signal components 22 of the demodulated measuring signal 14, extracted by the subsequent low-pass filtering. The bandwidth of the band-pass filter 19 and the cut-off frequency of the low-pass filter 21 are large enough to let through the frequency bands of the measuring signal 14 to be evaluated based on DAS and/or WMS.

Returning to FIG. 1, the useful information 23, 22 obtained by the low-pass filtering and demodulation are added in a summing unit 24 and then evaluated in a computing apparatus 25 based on DAS and/or in a further computing apparatus 26 based on WMS. The results 27, 28 of the DAS and WMS evaluations are added in a third computing apparatus 29 or combined with the aid of statistical signal processing in order to finally obtain the concentration of the gas component to be measured as a measurement result 16.

The WMS evaluation is performed, for example, at the second harmonics of the n (n≥1) frequencies of the low-frequency WMS modulation used. This entails n individual evaluations, which produce, for example, n curve profiles. In addition, the WMS evaluation can also be performed at the fundamental frequencies or further higher harmonics, which results in additional sets of n individual evaluations in each case. The n curve profiles within each individual set correlate and can be evaluated to form an intermediate result. The intermediate results from the different sets are then in turn combined, and in the simplest case added together.

The WMS evaluation can be expanded in that the low-frequency WMS modulation occurs at frequencies that are spaced apart from each other by twice the magnitude of the lowest additional frequency, i.e., when n=4, the frequencies: $f_{NF}$, $3f_{NF}$, $5f_{NF}$ and $7f_{NF}$. The WMS evaluation can then be performed both at the second harmonics of these frequencies, i.e. $2f_{NF}$, $6f_{NF}$, $10f_{NF}$ and $14f_{NF}$, and also at their sum and difference frequencies, i.e. $2f_{NF}$, $4f_{NF}$, $6f_{NF}$, $8f_{NF}$, $6f_{NF}$, . . . , $14f_{NF}$. This entails $2(2n-1)=14$ individual evaluations that produce 14 curve profiles. As mentioned above, due to the non-linear shape of the sampled absorption line, the measuring signal 14 contains not only the second harmonics of the frequencies used during the modulation, but also the sums and differences of these frequencies, which either coincide with the second harmonics or lie exactly halfway therebetween. The measuring signal components at the frequencies $2f_{NF}$, $4f_{NF}$, $6f_{NF}$, $8f_{NF}$, $6f_{NF}$, . . . $14f_{NF}$ each have the same profiles so that they are superimposed in a constructive way and so increase the evaluable signal energy from the absorption.

Figure 3:
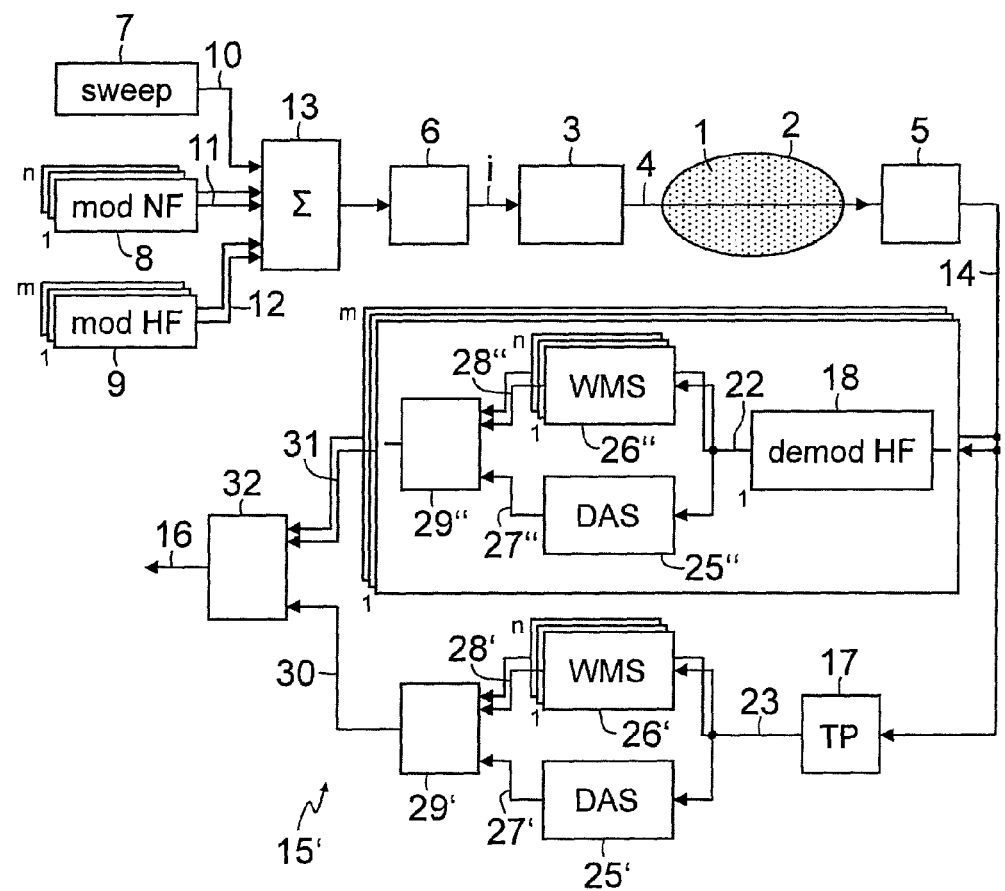
FIG. 3 a further exemplary embodiment of a gas analyzer in accordance with the invention.

FIG. 3 shows a further exemplary embodiment of the gas analyzer in accordance with the invention with an evaluation apparatus 15' modified compared to FIG. 1. The useful information 23, 22 obtained by filtering the measuring signal 14 via the low-pass filter 17 and by demodulation at the m different frequencies of the RF modulation are not, as in the case of the exemplary embodiment in FIG. 1, added and then evaluated, but are evaluated individually for the low-pass channel and each of the m RF demodulation channels in computing apparatuses 25', 25" based on DAS and further computing apparatuses 26', 26" based on WMS. Finally, the results 30, 31 of the different evaluations are combined in a computing unit 32, such as an adder, to form the measurement result 16.

Figure 4:
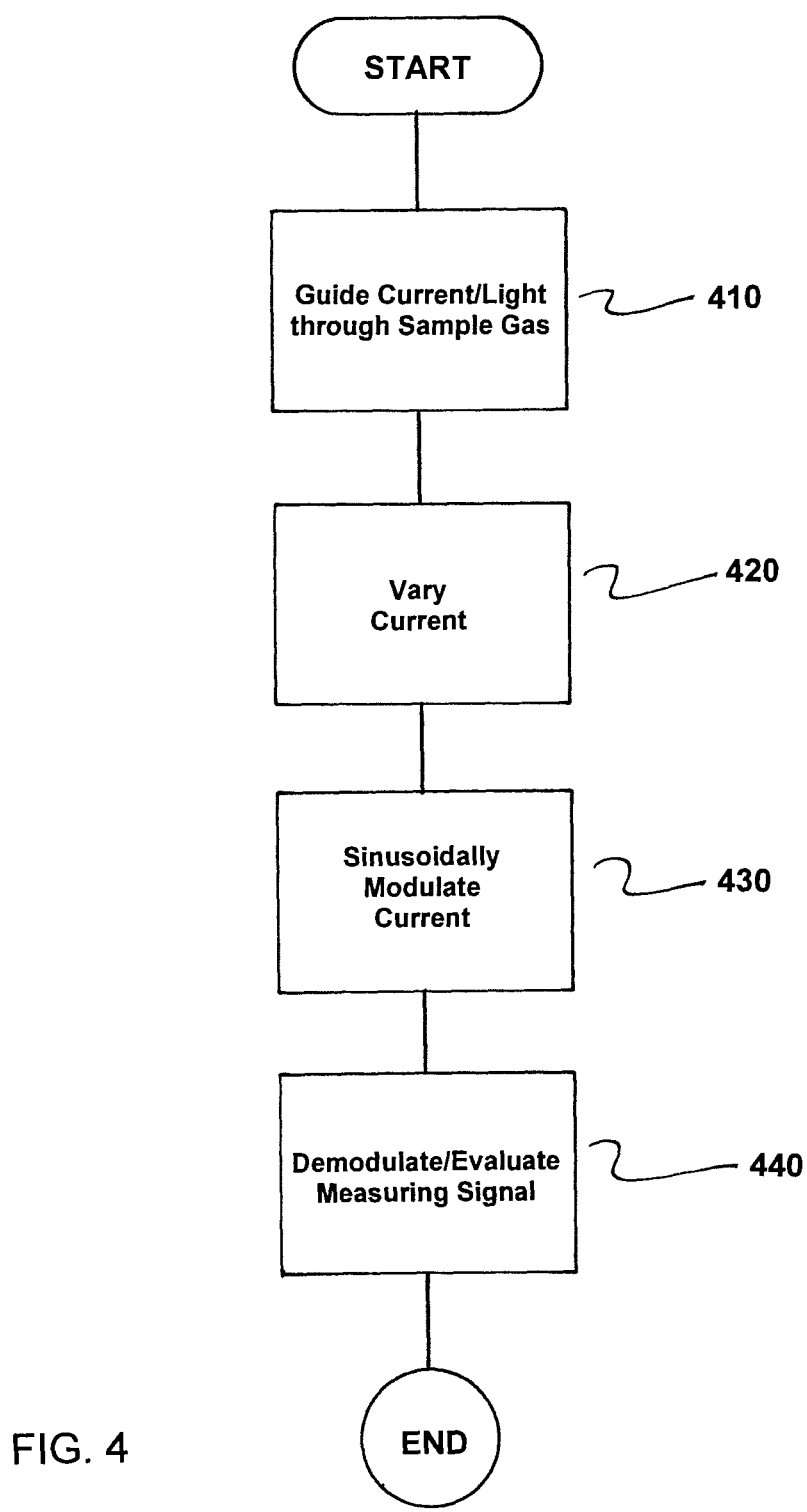
FIG. 4 is a flowchart of the method in accordance with the invention.

FIG. 4 is a flowchart of a method for measuring a concentration of a gas component in a sample gas (1) via a gas analyzer. The method comprises guiding a current (I) and light (4) generated by a wavelength tunable laser diode (3) through the sample gas (1) to a detector (5) to actuate a wavelength-tunable laser diode (3), as indicated in step 410.

Next, the current (I) is varied in periodically successive sampling intervals for a wavelength-dependent sampling of an absorption line of interest of the gas component, as indicated in step 420. The current (I) is now sinusoidally modulated with a predefined frequency and amplitude, as indicated in step 430. A measuring signal (14) generated by the detector (5) is now demodulated at a modulation frequency and an obtained demodulated measuring signal (22) is evaluated to form a measurement result (16), as indicated in step 440.

In accordance with the invention, the modulation frequency is selected as a function of properties of the wavelength-tunable laser diode (3) at a level high enough to ensure no wavelength modulation occurs and an amplitude of modulation is selected at the maximum level within and utilizing the linear control range of the wavelength-tunable laser diode (3).

While there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for measuring a concentration of a gas component in a sample gas via a gas analyzer, the method comprising:
    guiding a current (I) and light generated by a wavelength-tunable laser diode through the sample gas to a detector to actuate a wavelength-tunable laser diode;
    varying the current (I) in periodically successive sampling intervals for a wavelength-dependent sampling of an absorption line of interest of the gas component;
    modulating the current (I) sinusoidally at a predefined frequency and amplitude; and
    demodulating a measuring signal generated by the detector at a modulation frequency and evaluating an obtained demodulated measuring signal to form a measurement result;
    wherein the modulation frequency for the current is selected as a function of properties of the wavelength-tunable laser diode at a level which ensures no wavelength modulation occurs and an amplitude of modulation for the current is selected at a maximum level within and utilizing a linear control range of the wavelength-tunable laser diode.

2. The method as claimed in claim 1 wherein the current (I) of the wavelength-tunable laser diode is modulated with at least one further frequency, which is also selected at the level which ensures no wavelength modulation occurs;
    wherein modulation amplitudes within and utilizing the linear control range of the laser diode are selected at a maximum level;
    wherein the measuring signal generated by the detector is additionally demodulated at the frequency of the at least one further modulation; and
    wherein demodulated measuring signals obtained are one of (i) evaluated individually and then combined to form the measurement result and (ii) initially combined and then evaluated to form the measurement result.

3. The method as claimed in claim 2, wherein the method is based on direct absorption spectroscopy.

4. The method as claimed in claim 3, wherein measurements based on direct absorption spectroscopy and wavelength modulation spectroscopy are performed one of (i) simultaneously in each sampling interval and (ii) alternately in successive sampling intervals; and results of the measurements are linked by averaging to form the measurement result.

5. The method as claimed in claim 3, wherein, in cases of modulation with a plurality of additional frequencies, said frequencies are spaced apart by twice a magnitude of a lowest additional frequency; and wherein evaluation of the demodulated measuring signal based on wavelength modulation spectroscopy is performed at second harmonics of the plurality of additional frequencies and at least one of (i) a sum and (ii) difference frequencies of the plurality of additional frequencies.

6. The method as claimed in claim 1, wherein the method is based on direct absorption spectroscopy.

7. The method as claimed in claim 6, wherein measurements based on direct absorption spectroscopy and wavelength modulation spectroscopy are performed one of (i) simultaneously in each sampling interval and (ii) alternately in successive sampling intervals; and results of the measurements are linked by averaging to form the measurement result.

8. The method as claimed in claim 1, wherein the method is based on wavelength modulation spectroscopy; and wherein the current (I) of the wavelength-tunable laser diode is additionally modulated with a reduced amplitude and at least one additional frequency which is selected a reduced level which ensures wavelength modulation occurs.

9. The method as claimed in claim 8, wherein, in cases of modulation with a plurality of additional frequencies, said plurality of additional plurality of additional frequencies are spaced apart by twice a magnitude of a lowest additional frequency; and wherein evaluation of the demodulated measuring signal based on wavelength modulation spectroscopy is performed at second harmonics of the plurality of additional frequencies and at least one of (i) a sum and (ii) difference frequencies of the plurality of additional frequencies.

10. A gas analyzer for measuring a concentration of a gas component in a sample gas, comprising:
 a wavelength-tunable laser diode;
 a current source that feeds the wavelength-tunable laser diode with a current (I);
 a signal generator which controls the current source to vary the current (I) for wavelength-dependent sampling of an absorption line of interest of the gas component within periodically successive sampling intervals;
 a modulator apparatus which feeds the current source to modulate the current (I) sinusoidally with a predefined frequency and amplitude; means for guiding modulated light through the sample gas to a detector; and
 an evaluator which demodulates a measuring signal generated by the detector at a modulation frequency and evaluates an obtained demodulated measuring signal for generation of a measurement result; wherein the modulation apparatus is configured to perform the modulation with a frequency selected at a levels which ensures no wavelength modulation occurs; and
 wherein the modulation apparatus is further configured to perform modulation with an amplitude at a maximum level lying within a linear control range.

11. The gas analyzer as claimed in claim 10, wherein the modulation apparatus is further configured to modulate the current (I) of the wavelength-tunable laser diode with at least one further frequency, which is also selected at the level which ensures no wavelength modulation occurs;
 wherein modulation amplitudes are selected at a maximum level within and utilizing a linear control range of the wavelength-tunable laser diode;
 wherein the evaluation apparatus is configured to demodulate the measuring signal generated by the detector additionally at the frequency of the at least one further modulation and one of (i) evaluate the demodulated measuring signals obtained individually and then said demodulated measuring signals to form the measurement result and (ii) initially combine and then evaluate said demodulated measuring signals to form the measurement result.

12. The gas analyzer as claimed in claim 10, wherein the evaluation apparatus is configured to evaluate the demodulated measuring signal based on direct absorption spectroscopy.

13. The gas analyzer as claimed in claim 11, wherein the evaluation apparatus is configured to evaluate the demodulated measuring signal based on direct absorption spectroscopy.

14. The gas analyzer as claimed in claim 10, further comprising:
 a low-frequency modulation apparatus which controls the current source to additionally modulate the current (I) with a low amplitude and at least one additional frequency which is selected at a level which ensures wavelength modulation occurs;
 wherein the evaluation apparatus is configured to evaluate the demodulated measuring signal based on wavelength modulation spectroscopy.

* * * * *